US010603637B2

(12) United States Patent
Alexiou et al.

(10) Patent No.: US 10,603,637 B2
(45) Date of Patent: Mar. 31, 2020

(54) TWO-LAYER PHOTO-RESPONSIVE MEMBRANES

(71) Applicant: Trustees of Tufts College, Medford, MA (US)

(72) Inventors: Ayse Asatekin Alexiou, Arlington, MA (US); Samuel Thomas, Andover, MA (US); Papatya Kaner, Cambridge, MA (US); Xiaoran Hu, Somerville, MA (US)

(73) Assignee: Trustees of Tufts College, Medford, MA (US)

( * ) Notice: Subject to any disclaimer, the term of this patent is extended or adjusted under 35 U.S.C. 154(b) by 174 days.

(21) Appl. No.: 15/578,801

(22) PCT Filed: Jun. 1, 2016

(86) PCT No.: PCT/US2016/035145
§ 371 (c)(1),
(2) Date: Dec. 1, 2017

(87) PCT Pub. No.: WO2016/196542
PCT Pub. Date: Dec. 8, 2016

(65) Prior Publication Data
US 2018/0133657 A1 May 17, 2018

Related U.S. Application Data

(60) Provisional application No. 62/169,278, filed on Jun. 1, 2015.

(51) Int. Cl.
| | |
|---|---|
| *B01D 69/02* | (2006.01) |
| *A61M 5/14* | (2006.01) |
| *B60B 33/00* | (2006.01) |
| *B01D 61/14* | (2006.01) |
| *B01D 67/00* | (2006.01) |
| *B01D 69/10* | (2006.01) |
| *B01D 69/12* | (2006.01) |
| *B01D 71/62* | (2006.01) |
| *B01D 71/78* | (2006.01) |
| *C02F 1/44* | (2006.01) |

(52) U.S. Cl.
CPC .......... *B01D 69/02* (2013.01); *A61M 5/1415* (2013.01); *B01D 61/145* (2013.01); *B01D 67/0088* (2013.01); *B01D 69/10* (2013.01); *B01D 69/12* (2013.01); *B01D 71/62* (2013.01); *B01D 71/78* (2013.01); *B60B 33/0089* (2013.01); *B60B 33/0092* (2013.01); *C02F 1/444* (2013.01); *B01D 2325/04* (2013.01); *B01D 2325/20* (2013.01); *B01D 2325/34* (2013.01); *B01D 2325/36* (2013.01); *B01D 2325/38* (2013.01); *B60B 2200/26* (2013.01)

(58) Field of Classification Search
CPC .. B01D 61/145; B01D 67/0088; B01D 69/02; B01D 69/10; B01D 69/12; B01D 71/62; B01D 71/78; B01D 2325/04; B01D 2325/20; B01D 2325/34; B01D 2325/36; B01D 2325/38; B60B 33/0089; B60B 33/0092; B60B 2200/26; C02F 1/444; A61M 5/1415
See application file for complete search history.

(56) References Cited

U.S. PATENT DOCUMENTS

| 7,879,444 B2 | 2/2011 | Jiang et al. |
| 9,440,198 B2 | 9/2016 | McCloskey et al. |
| 2003/0099910 A1 | 5/2003 | Kim et al. |
| 2007/0151921 A1 | 7/2007 | Nakano et al. |
| 2013/0264287 A1 | 10/2013 | Zhang et al. |
| 2015/0273367 A1 * | 10/2015 | Tanaka ................ B01D 63/02 210/190 |

FOREIGN PATENT DOCUMENTS

| WO | WO 2007/127722 A2 | 11/2007 | |
| WO | WO-2014192432 A1 * | 12/2014 | ............ B01D 63/02 |

OTHER PUBLICATIONS

Chung, D.-J., Ito, Y., Imanishi, Y., "Preparation of Porous Membranes Grafted with Poly(spiropyran-containing methacrylate) and Photocontrol of permeability", J. Appl. Polymer Sci., 1994, 51, 2027-2033 (Year: 1994).*
Nayak, A., Liu, H., Belfort, G., "An Optically Reversible Switching Membrane Surface", Angew. Chem. Int. Ed. 2006, 45, 4094-4098 (Year: 2006).*
Chung et al "Preparation of Porous Membranes Grafted with Poly(Spiropyran-Containing Methacrylate) and Photocontrol of Permeability" Journal of Applied Polymer Science vol. 51, pp. 2027-2033, 1994.
Nayak et al "An Optically Reversible Switching Membrane Surface" Angewandte Chemie International Edition vol. 45, pp. 4094-4098, 2006.
Park et al "Photocontrolled Gating by Polymer Brushes Grafted on Porous Glass Filter," Macromolecules vol. 31, pp. 2606-2610, 1998.
Prince et al "Self-Cleaning Metal Organic Framework (MOF) Based Ultra Filtration Membranes—A Solution to Bio-Fouling in Membrane Separation Processes" Scientific Reports vol. 4, pp. 1-9, 2014.

(Continued)

*Primary Examiner* — James C Goloboy
(74) *Attorney, Agent, or Firm* — Foley Hoag LLP

(57) ABSTRACT

A two-layer photo-responsive membrane including a polymer layer and a support layer, the polymer layer being disposed on a surface of the support layer. The polymer layer is formed of a graft copolymer that contains a hydrophobic backbone and multiple side chains, the side chains each consisting of repeat units that switch between a hydrophobic form and a hydrophilic form upon exposure to a light of a specific wavelength. The polymer layer has a molecular weight cut-off of 3,000 to 250,000 Daltons and a thickness of 50 nm to 10 μm; and the support layer has a molecular weight cut-off of 50 to 250,000 Daltons. Also disclosed is a method of preparing this two-layer photo-responsive membrane.

28 Claims, No Drawings

(56) References Cited

OTHER PUBLICATIONS

Scholler et al "From Membrane to Skin: Aqueous Permeation Control Through Light-Responsive Amphiphilic Polymer Co-Networks" Advanced Functional Materials vol. 24, pp. 5194-5201, 2014.

Wagner et al "Light-Induced Wettability Changes on Polymer Surfaces" Polymer vol. 55, pp. 3436-3453, 2014.

You et al "Fouling Removal of UF Membrane with Coated $TiO_2$ Nanoparticles Under UV Irradiation for Effluent Recovery During TFT-LCD Manufacturing" International Journal of Photoenergy vol. 2013, pp. 1-8, 2013.

\* cited by examiner

TWO-LAYER PHOTO-RESPONSIVE MEMBRANES

BACKGROUND

Membrane filtration is an important technique used in water purification and wastewater treatment. Indeed, filtration membranes have drawn much attention for their unique applications in many areas including, among others, beverage, dairy, pharmaceuticals, and food industry.

There are three major issues associated with use of filtration membranes: low permeability, poor selectivity, and fouling. Low permeability necessitates operation at high pressures and use of larger membrane areas, resulting in low energy efficiency and high cost. On the other hand, poor selectivity, due to lack of desired pore sizes, does not meet specific separation needs. Finally, membrane fouling, i.e., loss of permeability resulting from adsorption and adhesion of feed components, leads to low efficiency, high energy use, and short membrane lifespans.

There is a need to develop new membranes that are highly permeable, highly selective, and fouling resistant.

SUMMARY

This invention relates to a photo-responsive membrane containing a graft copolymer for filtering a liquid. The photo-responsive membrane exhibits an unexpectedly high water permeance. It also unexpectedly exhibits great selectivity, fouling resistance, and high capability of self-cleaning.

In one aspect, the present invention is a two-layer photo-responsive membrane that includes a polymer layer and a support layer. The polymer layer being disposed on a surface of the support layer is formed of a graft copolymer that contains a hydrophobic backbone and multiple side chains, the side chains each consisting of repeat units that switch between a hydrophobic form and a hydrophilic form upon exposure to a light of a specific wavelength. In addition, the polymer layer has a molecular weight cut-off of 3,000 to 250,000 Daltons and a thickness of 50 nm to 10 μm; and the support layer has a molecular weight cut-off of 50 to 250,000 Daltons.

One example of the polymer layer has a molecular weight cut-off of 3,000 to 100,000 Daltons (e.g., 3,000 to 50,000 Daltons) and a thickness of 100 nm to 2 μm (e.g., 200 nm to 1 μm). The support layer can have a pore size of 5 μm or lower (e.g., 2-5 nm).

An exemplary support layer has a molecular weight cut-off lower than that of the polymer layer, but higher than 50 Daltons. In another example, the support layer has a molecular weight cut-off higher than that of the polymer layer, but lower than 250,000 Daltons (e.g., 100,000-250,000 Daltons).

The graft copolymer typically has a molecular weight of 1,000 to 10,000,000 Daltons. Preferably, it has a molecular weight of 5,000 to 1,000,000 Daltons; and more preferably, 10,000 to 500,000 Daltons.

The hydrophobic backbone can be formed of acrylonitrile, vinylidene fluoride, acrylate, methacrylate, or a combination thereof. Examples of the hydrophobic backbone include polyacrylonitrile and poly(vinylidene fluoride).

The side chains each typically contain spiropyran, merocyanine, or a combination thereof. In one example, the side chains each contain repeat units formed of spiropyran methacrylate.

The side chains can have 3-40 repeat units (e.g., 3-10 repeat units).

One example of the two-layer photo-responsive membrane has a water permeance of 20 $Lm^{-2} h^{-1} bar^{-1}$ or lower (e.g., 15 $Lm^{-2} h^{-1} bar^{-1}$), a bovin serum albumin rejection of 90-97%, and a molecular weight cut-off of 30,000-75,000 Daltons.

In another aspect, this invention is a method of preparing a two-layer photo-responsive membrane. The method include the following steps: (i) providing a graft copolymer that contains a hydrophobic backbone and multiple side chains, the side chains each consisting of one or more repeat units that switch between a hydrophobic form and a hydrophilic form upon exposure to a light of specific wavelength; and (ii) depositing onto a support layer a layer of the graft copolymer to form a two-layer photo-responsive membrane.

The details of the invention are set forth in the description below. Other features, objects, and advantages of the invention will be apparent from the following detailed description of several embodiments, and also from the appending claims.

DETAILED DESCRIPTION

Disclosed in detail herein is a two-layer photo-responsive membrane containing a graft copolymer for filtering a liquid. The membrane includes a support layer and a polymer layer formed of a graft copolymer. The graft copolymer contains a hydrophobic backbone and a plurality of side chains.

The hydrophobic backbone can be formed from acrylonitrile, vinylidene fluoride, acrylate, methacrylate, or a combination thereof.

The side-chains are made of repeat units that switch between a hydrophobic form and a hydrophilic form upon exposure to a light of a specific wavelength. They can be selected from numerous photo-responsive polymers well known in the field.

An exemplary photo-responsive side-chain contains repeat units that undergo a photo-reversible isomerization, as shown below, from a neutral, hydrophobic form, i.e., photochromic nitrospiropyran or spiropyran, to a zwitterionic, hydrophilic form, i.e., merocyanine, upon exposure to an ultraviolet (UV) light. The repeat units switch back to their spiropyran form upon exposure to a visible light, upon heating, or in a polar solvent.

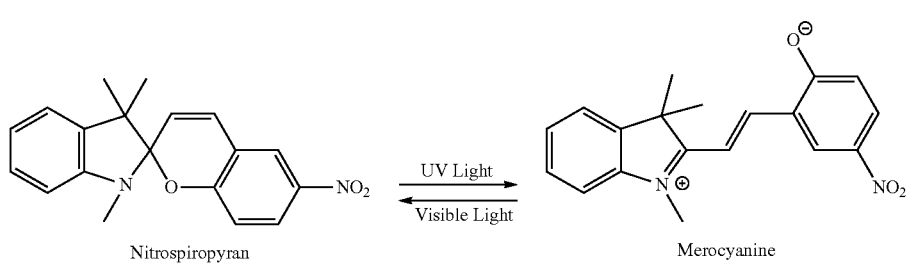

Nitrospiropyran     Merocyanine

The graft copolymer, being comb-shaped, must be insoluble in water, even upon conversion of the photo-responsive repeat units to their hydrophilic form, for the membrane to function.

Depending on the pore size of the support layer, the polymer layer serves two functions: imparting membrane selectivity and imparting self-cleaning capability.

In one example, the support layer contains large pores (e.g., average pore size >10 nm) and has a molecular weight cut-off higher than that of the polymer layer, but lower than 250,000 Daltons (e.g., 100,000-250,000 Daltons). This polymer layer serves to control the selectivity of the membrane.

In another example, the support layer includes pores with small effective pore sizes and has a molecular weight cut-off lower than that of the polymer layer, but higher than 50 Daltons, in which the polymer layer serves as a coating layer to impart self-cleaning capability of the membrane.

The self-cleaning capability, which arises from the switch between a hydrophobic form and a hydrophilic form of the side chains, leads to two effects, namely, making membrane surfaces more hydrophilic and enhancing fouling resistance due to swelling of the side chains. It is unexpectedly observed that a graft copolymer with longer side chains shows lower self-cleaning capability than that with shorter ones. The graft copolymer can contain side chains having 3-40 repeat units. Preferably, the side chains each have 3-10 repeat units (e.g., 8 repeat units).

Also within the scope of this invention is a method of preparing a two-layer photo-responsive membrane.

An illustrative protocol for producing the two-layer photo-responsive membrane is set forth below.

First, a bromo- or chloro-containing copolymer is synthesized by using a standard method of polymerizing a hydrophobic monomer (e.g., acrylonitrile) and a bromo- or chloro-containing monomer. A graft copolymer is subsequently produced via an atom transfer radical polymerization (ATRP) of the bromo- or chloro-containing copolymer and a monomer containing a photo-responsive functional group.

A polymer layer is then formed by coating a solution of the graft copolymer thus generated onto a porous support layer using methods well known in the field (e.g., doctor blade coating and spray coating). A two-layer photo-responsive membrane is thus produced.

An exemplary photo-responsive membrane, which is prepared following the above protocol, contains the graft copolymer that switches from a hydrophobic spiropyran form to a hydrophilic merocyanine form upon exposure to a UV light, as evidenced by a color change from yellowish white to purple. The hydrophilic merocyanine form is preserved, when the membrane is stored in water, for an extended period of time, up to days, as evidenced by the lasting of the purple color. Upon exposure to a visible light, the membrane switches back to a yellowish white color, indicating the hydrophobic spiropyran form. This phenomenon can be repeated at least twice.

In one example, the photo-responsive membrane unexpectedly exhibits a high water permeance up to 20 Lm$^{-2}$ h$^{-1}$ bar$^{-1}$ (e.g., 15 Lm$^{-2}$ h$^{-1}$ bar$^{-1}$) and a high bovin serum albumin rejection of 90-97%.

In one study of self-cleaning capability, the photo-responsive membrane can fully recover its water permeance even after fouled to greater than greater than 95% upon exposure to a UV light.

Without further elaboration, it is believed that one skilled in the art can, based on the above description, utilize the present invention to its fullest extent. The following specific examples are, therefore, to be construed as merely illustrative, and not limitative of the remainder of the disclosure in any way whatsoever. All publications cited herein are incorporated by reference.

EXAMPLE 1

Preparation of a Graft Copolymer (ACN-r-AEMA)-g-SPMA

A graft copolymer (ACN-r-AEMA)-g-SPMA was synthesized as follows.

A reaction scheme utilized for this synthesis is shown below.

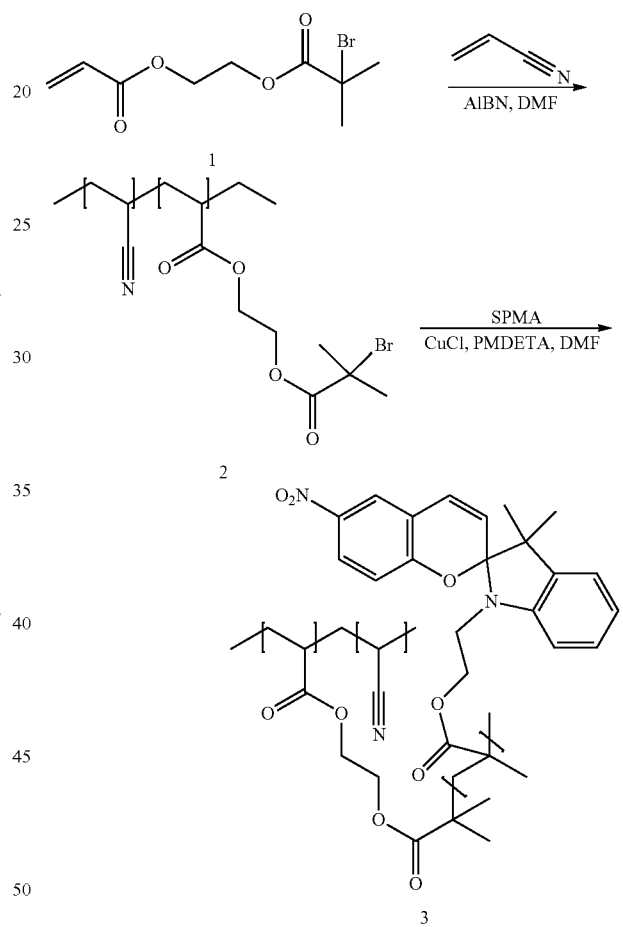

Compound 1 (AEMA) and 1'-(2-Methacryloyloxyethyl)-3',3'-dimethyl-6-nitrospiro(2H-1benzopyran-2,2'-indoline) (SPMA) were synthesized following previous reports. See Friedle et al., *Angew Chem. Int. Edit,* 2010, 49 (43), 7968-7971; and Jones et al., *Polym. Chem.,* 2011, 2 (3), 572-574.

To synthesize compound 2, a macro-initiator labeled as ACN-r-AEMA, compounds AEMA and acrylonitrile (ACN) were copolymerized using a free radical polymerization. Namely, 0.1 g of AEMA, 2.5 g of ACN (feeding ratio=1:125 by mole), and 5.0 mg azobisisobutyronitrile (AIBN) were added to 10 mL of N,N-dimethylformamide (DMF) in a 25 mL three neck round bottom flask. After fully dissolving the starting materials, the reaction mixture thus formed was purged with argon for at least 20 minutes and then stirred at 60° C. overnight. The reaction mixture was first precipitated in methanol, followed by filtration to collect a solid. The solid collected was redissolved in about 10 mL of DMF and precipitated in a 1:1 mixture of acetone and methanol. After filtration, the polymer thus obtained was dried under vacuum over two days. 1.3 g of a copolymer (compound 2) was obtained as a white solid (yield: 50%). It was characterized by $^1$H NMR spectrum.

The ACN-r-AEMA copolymer was found to contain about 1 brominated unit per 144 ACN repeat units.

To synthesize (ACN-r-AEMA)-g-SPMA (compound 3), ACN-r-AEMA, SPMA, and N,N,N',N',N"-pentamethyldiethylenetriamine (PMDETA) were dissolved in DMF to make a 10~20% solution (by w.t) in a 100 mL Schlenk tube (Two batches of the graft copolymer were prepared; and compositions of the reaction mixtures for each are shown in the Table 1 below). After three freeze-pump-thaw cycles, the solution was frozen with liquid nitrogen, and CuCl was carefully added into the Schlenk tube under argon protection. The tube was pumped for another 10 minutes, after which the reaction was thawed, and stirred overnight at 65° C. The solution was exposed to the atmosphere for an hour to oxidize the copper salt, which was then removed by passing the solution through an alumina column. The polymer was precipitated in methanol. The solid thus collected was extracted against methanol over two days. After filtration, the purple solid collected was dried under vacuum over two nights.

non-solvent bath for 1 hour to precipitate the copolymer out. A non-solvent, isopropanol, was selected for its low diffusivity with DMSO to prevent the formation of a porous coating.

Film thickness and morphology were determined by examining freeze-fractured cross-sections of the membrane thus prepared using a scanning electron microscope (SEM, Phenom G2 Pure Tabletop SEM).

It was observed that a coating layer being dense (i.e. without macroscopic pores) had a thickness of about 1 micrometer for the photo-responsive membrane.

EXAMPLE 3

Photo-Responsive Switching Study of a TFC Membrane with Photo-Responsive Graft Copolymer A study was performed to assess the switching of the SPMA side chains between a spiropyran (SP) form and a merocyanine (MC) form in the copolymer selective layers of the membranes prepared in Example 2. Results of the study were recorded by visual inspection and FTIR spectroscopy.

The membrane surface was exposed to a UV light of 254 nm wavelength for 2 hours using a UV lamp (UVP Compact and Handheld) equipped with a 254/356 nm split tube. This SP-dominated surface, after exposed to a visible light for 2 hours, turned yellowish, indicating that the membrane surface has a MC configuration of the side chains. The mem-

TABLE 1

Preparation of a graft copolymer

| Graft copolymer | Reaction mixture composition | | | | | | Copolymer composition | |
|---|---|---|---|---|---|---|---|---|
| | ACN-r-AEMA backbone | SPMA | CuCl | PMDETA | Reaction time | Yield | 2:SPMA weight ratio | Br:SMPA mole ratio |
| 1:8 (ACN-r-AEMA)-g-SPMA | 0.55 g | 0.55 g | 6.9 mg | 12 mg | 14 h | 0.85 g | 70:30 | 1:8 |
| 1:24 (ACN-r-AEMA)-g-SPMA | 0.43 g | 0.77 g | 5.3 mg | 30 mg | 20 h | 1.0 g | 40:60 | 1:21 |

The copolymer composition and side-chain length was determined using the $^1$H-NMR spectra of the backbone and side-chains. The ratio of their peaks in $^1$H-NMR spectra, and the ACN:Br ratio of the initial ACN-r-AEMA composition were used to calculate the final graft copolymers' composition, as shown in Table 1.

EXAMPLE 2

Preparation of a Thin Film Composite (TFC) Membrane with Photo-Responsive Graft Copolymer A photo-responsive membranes was prepared by coating a porous support membrane with the graft copolymer described in Example 1.

The copolymer (0.75 g) was dissolved in dimethyl sulfoxide (DMSO, 5 ml) by stirring overnight at room temperature to form a copolymer solution. A two-layer membrane was produced by coating a thin layer of the copolymer solution onto a commercial ultrafiltration (UF) membrane using a rolling rod with 6 micrometer opening. PVDF400 ultrafiltration membrane, purchased from Sepro Inc. (Oceanside, Calif.), was used as the base membrane. After coating, the two-layer membrane was immersed into a brane coated with 1:8 (ACN-r-AEMA)-g-SPMA was found to respond faster to both visible and UV irradiation than that coated with 1:24 (ACN-r-AEMA)-g-SPMA.

ATR-FTIR was used to characterize the photo-induced conversion of SP to MC on membranes. The infrared spectra were recorded using a Jasco FTIR-6200 Spectrometer (Jasco Instruments, Tokyo, Japan), equipped with a deuterated triglycine sulfate detector and a multiple-reflection, horizontal MIRacle ATR accessory. The spectra were analyzed using a SpectraManager software in absorption mode at 4 cm$^{-1}$ resolution with 256 scans between 2000-600 cm$^{-1}$. Background absorption was subtracted from the sample spectra to establish baseline.

The ATR-FTIR spectra were first collected on the as-coated membranes, followed by measurements on the same swatch upon UV and visible light irradiation in two cycles. Changes in fingerprint IR peaks pertinent to ring-closed SP and ring-opened MC forms upon respective UV and visible light treatment confirmed the structural difference between the two forms at a molecular level. Bands of particular importance are listed in Table 2 below. Note that peak assignments were adopted from previous works. See Fries et al., *Analytical chemistry*, 2010, 82 (8), 3306-3314; and Dattilo et al., *Langmuir*, 2007, 23 (26), 12945-12950.

TABLE 2

Important FTIR frequencies of (ACN-r-AEMA)-g-SPMA polymer in spiropyran and merocyanine forms.

| Assignment | Spiropyran (SP) Wavenumbers (cm$^{-1}$) | Merocyanine (MC) Wavenumbers (cm$^{-1}$) |
|---|---|---|
| N-C$_{spiro}$-O | 956 | — |
| C—C—N bend | 1027 | — |
| C—O—C ether asym stretch | 1090 | — |
| C—C=C asym stretch | 1482 | 1482 |
| NO$_2$ sym stretch | 1518 | 1518 |

The SP bands of N—C$_{spiro}$—O at 956 cm$^{-1}$ and C—O—C at 1090 cm$^{-1}$ increased significantly in intensity after visible light irradiation. It was also observed that both the as-coated and UV-irradiated surfaces consisted mainly of MC chains.

EXAMPLE 4

Water Permeability of a TFC Membrane with Photo-Responsive Graft Copolymer

Pure water permeances of the membranes described in Example 2 were measured as follows.

First, the water permeance through the as-coated membrane was measured. Then, the same membrane swatch was subjected to two successive UV (2 hours) and visible light (2 hours) exposure cycles, where the pure water permeance was measured after each exposure. All permeability tests were conducted with an Amicon 8010 stirred, dead-end filtration cell (Millipore) with a cell volume of 10 mL and an effective filtration area of 4.1 cm$^2$, attached to a 3.5-L dispensing vessel. The cell was stirred at 500 rpm using a stir plate under a pressure of 10 psi (0.07 MPa). A Scout Pro SP401 balance connected to a Dell laptop was used to automatically measure the permeate weight every 30 seconds using TWedge 2.4 software (TEC-IT, Austria). The permeate flow occured one droplet at a time. Hence the measured volume at each data point varied by 1-2 droplets amounting to 0.05-0.1 ml. The membrane was first allowed to stabilize by passing deionized (DI) water through it for 2-3 hours, until the flux stabilized to a constant value for over half an hour. This procedure was repeated after each light exposure step to measure the water permeance of the light-processed membranes.

A sharp increase was observed in the water permeance of the copolymer containing 8-repeat-unit side-chains upon UV irradiation. The water permeance remained essentially the same after repeated first UV exposure. It was unexpectedly observed that the permeability of the membrane, which was coated with the copolymer containing 8-repeat-unit side-chains, was at least twice the permeability of the membrane coated with the copolymer containing 24-repeat-unit side-chains.

EXAMPLE 5

Protein Rejection, Fouling and Self-Cleaning Membrane Upon Light Exposure

The rejection, fouling, and self-cleaning properties of the photo-responsive membrane described in Example 2 were studied using dead-end stirred cell filtration tests. The filtration system described in Example 4 was also used in testing the protein rejection, fouling, and self-cleaning properties of the photo-responsive membrane. The model foulant solution comprised 1 g/L bovine serum albumin (BSA, 66.5 kDa) in phosphate buffer saline (PBS, pH 7.4). All filtration runs were conducted under 10 psi (0.07 MPa) pressure. First, the membrane was allowed to stabilize by passing deionized (DI) water through it for 2-3 hours, until the flux stabilized to a constant value for over half an hour. The end of the stabilization period was taken to be the zero time point in the filtration plots. Then, the BSA fouling test was conducted in three steps: (1) filtering DI water to determine the initial flux, (2) filtering bovine serum albumin (BSA, 66.5 kDa) foulant solution to simulate protein fouling, and (3) filtering DI water again to compare the water permeance before and after BSA fouling. The protein concentrations in feed and permeate were quantified by measuring the UV absorbance at 280 nm utilizing a Thermo Scientific Genesys 10S UV-Vis spectrophotometer equipped with a high-intensity xenon lamp and dual-beam optical geometry. For testing the fouling reversibility, i.e., the self-cleaning performance upon light stimulus, three-step BSA fouling cycle was followed by UV exposure on the fouled membrane surface and then re-filtration of DI water to determine the consequent water permeability. The BSA fouling procedure combined with the self-cleaning testing was conducted four times on the photo-responsive membrane, before and after exposure to a UV or visible light successively after each fouling cycle.

It was observed that both the membranes prepared in Example 1 each exhibited unexpectedly high bovin serum albumin rejection rates of 90-97%, even after four fouling cycles.

The membrane formed of a graft copolymer containing 8-repeat-unit side-chains unexpectedly showed essentially complete self-cleaning performance, as indicated by the observation that even after three cycles of protein fouling, the water permeability was increased by UV exposure to a value higher than its initial value, which was consistent with the increase in pure water permeability upon first exposure to UV light described in Example 4. In addition, visible light treatment also offered partial recovery of the permeability. On the other hand, after two fouling cycles, the membrane formed of a graft copolymer containing 24-repeat-unit side-chains did not completely recover its initial permeability. The water flux of this membrane slowly declined after each following fouling cycle.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

Further, from the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

The invention claimed is:

1. A two-layer photo-responsive membrane for filtering a liquid, comprising:
   a support layer, wherein the support layer has a molecular weight cut-off of 50 to 250,000 Daltons; and
   a polymer layer formed of a graft copolymer that comprises a hydrophobic backbone and a plurality of side chains; wherein the polymer layer has a molecular weight cut-off of 3,000 to 250,000 Daltons, and a thickness of 100 nm to 2 µm;

each of the side chains consists of one or more repeat units that switch between a hydrophobic form and a hydrophilic form upon exposure to a light of a specific wavelength; and the polymer layer is disposed on a surface of the support layer.

2. The membrane of claim 1, wherein the graft copolymer has a number-average molecular weight of 1,000 to 10,000,000 Daltons.

3. The membrane of claim 2, wherein the graft copolymer has a number-average molecular weight of 5,000 to 1,000,000 Daltons.

4. The membrane of claim 3, wherein the graft copolymer has a number-average molecular weight of 10,000 to 500,000 Daltons.

5. The membrane of claim 1, wherein the polymer layer has a molecular weight cut-off of 150,000 Daltons or lower.

6. The membrane of claim 5, wherein the polymer layer has a molecular weight cut-off of 100,000 Daltons or lower.

7. The membrane of claim 6, wherein the polymer layer has a molecular weight cut-off of 50,000 Daltons or lower.

8. The membrane of claim 1, wherein the support layer has a molecular weight cut-off smaller than that of the polymer layer.

9. The membrane of claim 1, wherein the support layer has a molecular weight cut-off greater than that of the polymer layer.

10. The membrane of claim 1, wherein the hydrophobic backbone is formed from acrylonitrile, vinylidene fluoride, an acrylate, a methacrylate, or a combination thereof.

11. The membrane of claim 1, wherein each of the side chains comprises spiropyran or merocyanine, or a combination thereof.

12. The membrane of claim 11, wherein each of the side chains comprises repeat units formed from spiropyran methacrylate.

13. The membrane of claim 11, wherein each of the side chains comprises 3-40 repeat units.

14. The membrane of claim 13, wherein the membrane has a water permeance of 20 $Lm^{-2} h^{-1} bar^{-1}$ or lower, a bovine serum albumin rejection of 90-97%, and a molecular weight cut-off of 30,000-75,000 Daltons.

15. A two-layer photo-responsive membrane for filtering a liquid, comprising:

a support layer, wherein the support layer has a molecular weight cut-off of 50 to 250,000 Daltons; and a polymer layer formed of a graft copolymer that comprises a hydrophobic backbone and a plurality of side chains; wherein the polymer layer has a molecular weight cut-off of 3,000 to 250,000 Daltons, and a thickness of 50 nm to 10 µm;

the hydrophobic backbone is formed from acrylonitrile, vinylidene fluoride, an acrylate, a methacrylate, or a combination thereof;

each of the side chains consists of one or more of repeat units that switch between a hydrophobic form and a hydrophilic form upon exposure to a light of a specific wavelength; and the polymer layer is disposed on a surface of the support layer.

16. The membrane of claim 15, wherein the graft copolymer has a number-average molecular weight of 1,000 to 10,000,000 Daltons.

17. The membrane of claim 16, wherein the graft copolymer has a number-average molecular weight of 5,000 to 1,000,000 Daltons.

18. The membrane of claim 17, wherein the graft copolymer has a number-average molecular weight of 10,000 to 500,000 Daltons.

19. The membrane of claim 15, wherein the polymer layer has a molecular weight cut-off of 150,000 Daltons or lower.

20. The membrane of claim 19, wherein the polymer layer has a molecular weight cut-off of 100,000 Daltons or lower.

21. The membrane of claim 20, wherein the polymer layer has a molecular weight cut-off of 50,000 Daltons or lower.

22. The membrane of claim 15, wherein the polymer layer has a thickness of 100 nm to 2 µm.

23. The membrane of claim 15, wherein the support layer has a molecular weight cut-off smaller than that of the polymer layer.

24. The membrane of claim 15, wherein the support layer has a molecular weight cut-off greater than that of the polymer layer.

25. The membrane of claim 15, wherein each of the side chains comprises spiropyran or merocyanine, or a combination thereof.

26. The membrane of claim 25, wherein each of the side chains comprises repeat units formed from spiropyran methacrylate.

27. The membrane of claim 25, wherein each of the side chains comprises 3-40 repeat units.

28. The membrane of claim 27, wherein the membrane has a water permeance of 20 $Lm^{-2} h^{-1} bar^{-1}$ or lower, a bovine serum albumin rejection of 90-97%, and a molecular weight cut-off of 30,000-75,000 Daltons.

* * * * *